United States Patent [19]

Littorin

[11] 4,010,740
[45] Mar. 8, 1977

[54] SPECULUM

[75] Inventor: Ove Gustav Littorin, Stockholm, Sweden

[73] Assignee: ABM-Mavello AB, Stockholm, Sweden

[22] Filed: Apr. 21, 1976

[21] Appl. No.: 678,759

[30] Foreign Application Priority Data

Apr. 21, 1975 Sweden .......................... 7504607

[52] U.S. Cl. .................................. 128/17; 128/345
[51] Int. Cl.² ...................... A61B 1/32; A61M 29/00
[58] Field of Search ................... 128/11, 13, 16, 17, 128/18, 22, 23, 3, 341, 345

[56] References Cited

UNITED STATES PATENTS

| 3,528,409 | 9/1970 | Bruder | 128/17 |
|---|---|---|---|
| 3,568,665 | 3/1971 | Littorin et al. | 128/17 |
| 3,702,606 | 11/1972 | Barnard | 128/17 |
| 3,890,961 | 6/1975 | Moore et al. | 128/17 |

Primary Examiner—Robert W. Michell
Assistant Examiner—Henry S. Layton
Attorney, Agent, or Firm—Oblon, Fisher, Spivak, McClelland & Maier

[57] ABSTRACT

A speculum for examining body cavities comprises two angle pieces, each having a generally U-shaped cross-section along substantially its whole length, and consequently troughed-like legs, both angle pieces with their troughs facing each other being removably connectable to each other with side portions thereof on either side of the speculum overlapping each other to form a pivot portion from which the four legs extend, respective legs of the angle pieces being movable together or apart by means of one pair of legs comprised of a leg of each angle piece, serving as handles for operating the other pair, and characterized in that both angle pieces are identically alike and that in the area of the pivot portion, each has on one side a pin and on the opposite side a hole, the hole in each angle piece being made to accommodate the pin of the opposing angle piece.

8 Claims, 8 Drawing Figures

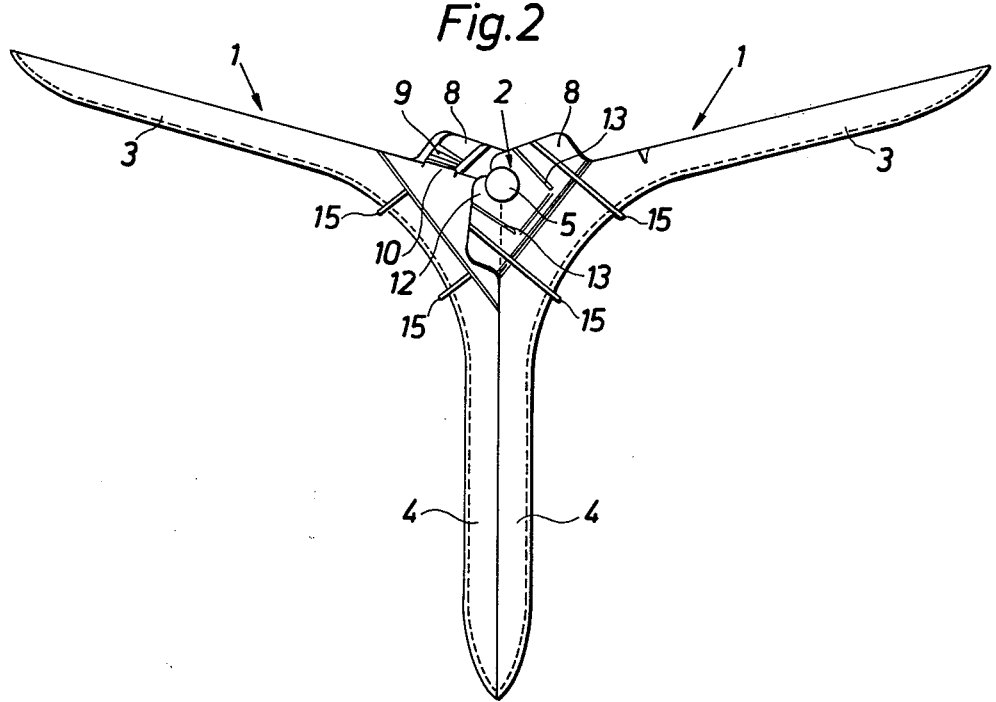
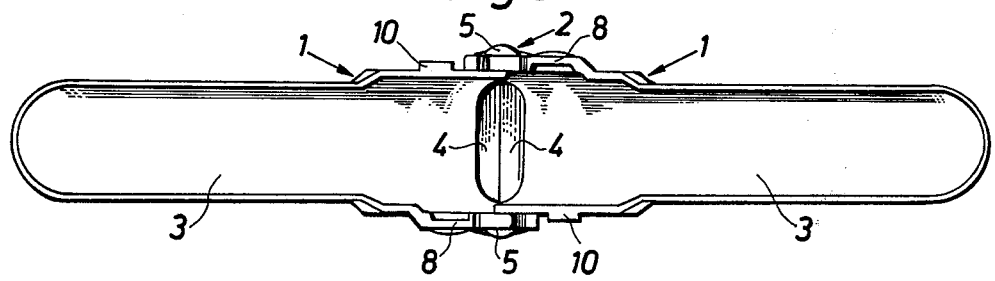
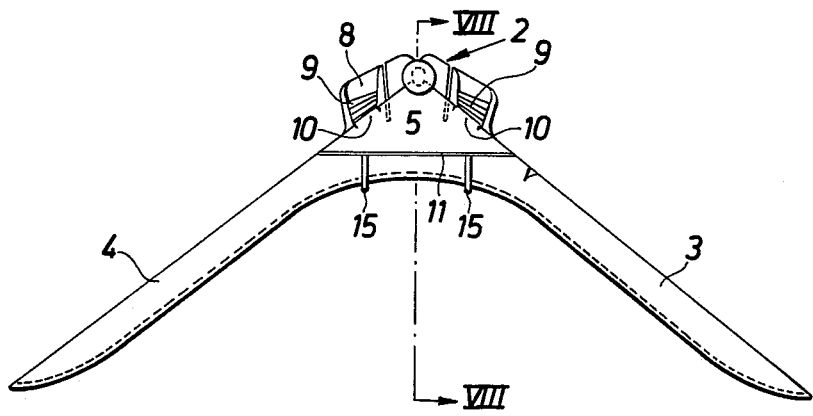

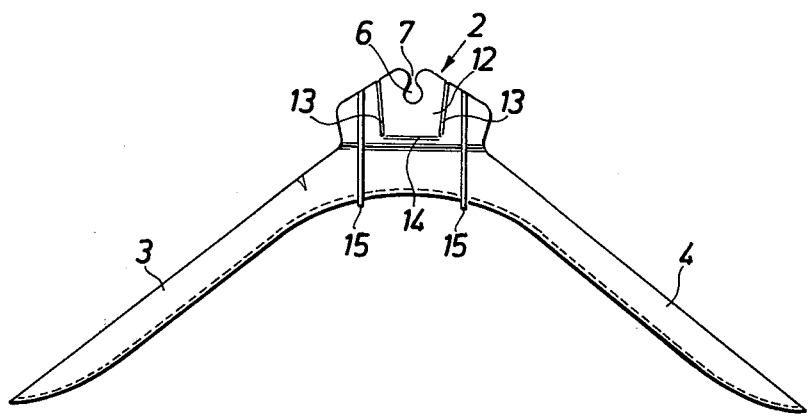
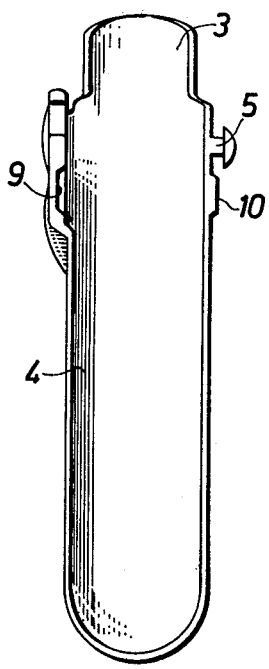
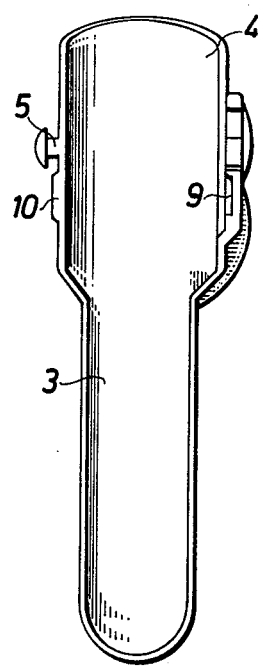
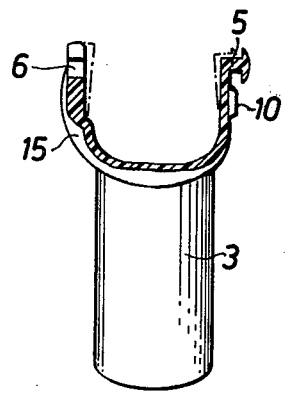

SPECULUM

BACKGROUND OF THE INVENTION

1. Field of the Invention

The present invention relates to a speculum which is adapted for investigating bodily cavities and consists of two angle pieces. Each angle piece has a generally U-shaped cross-section for substantially the whole of its length, and consequently troughed legs of which one is to advantage narrower than the other. Both angle pieces are made mutually removably connectable, with opposing troughs and with side portions of the angle pieces overlapping each other on either side to form a pivotal portion, from which four legs project, capable of being brought together or moved apart in pairs, with one pair of legs (one leg on each angle piece) serving as handles for operating the other pair. In relation to its field of use, the speculum may, for example, constitute a vaginal speculum, and ear speculum or a proctoscope.

2. BRIEF DESCRIPTION OF THE PRIOR ART

A speculum of the kind described above is previously known, e.g. from the British patent specification 1,234,590, and has one angle piece shaped with projecting portions on either side to form a pivotal portion, both side portions engaging round the second angle piece of the speculum, the second angle piece having an outwardly directed pin on either side for co-action with a hole in an adjacent side portion of the first angle piece.

A drawback with this known speculum is that it requires production and storage of two differently made angle pieces. A further drawback is that it has been necessary to make the joint as a sliding joint, the hole in the respective side portion being an elongate hole, to enable releasing angular location locking means arranged between the angle pieces, operation thereby being less positive, and the ends cannot always be kept in mutual conformity, while displacement in the sliding pivot can cause irritating nipping of tissue.

SUMMARY OF THE INVENTION

The object of the invention is to provide a speculum of the type set forth in the introduction, although improved for avoiding the aforementioned drawbacks. The foregoing object is achieved through the provision of a speculum which according to the present invention put together from two identically similar angle pieces, and allows the use of a simple and reliable pivot, even in an embodiment having locking means for fixing angular position. The pivot can also be made with small space requirements.

BRIEF DESCRIPTION OF THE DRAWINGS

Various other objects, features and attendant advantages of the present invention will be more fully appreciated as the same becomes better understood from the following detailed description of a preferred embodiment of a vaginal speculum according to the invention, when considered in connection with the appended drawings, wherein:

FIG. 2 is a side view of the same speculum with two of the legs moved together into the introductory position, both the remaining ones being at an angle to each other and serving as handles;

FIG. 3 is an end view of the speculum according to FIG. 2;

FIG. 4 is a side view of an angle piece for the speculum;

FIG. 5 is a side view of the same angle piece seen from the opposite side;

FIG. 6 is a view in a direction towards the open trough of one of the legs of the angle piece;

FIG. 7 is a view in a direction towards the open trough of the second leg of the angle piece;

FIG. 8 shows a section on the line VIII — VIII in FIG. 4.

DETAILED DESCRIPTION OF THE PREFERRED EMBODIMENT

Figure 1:
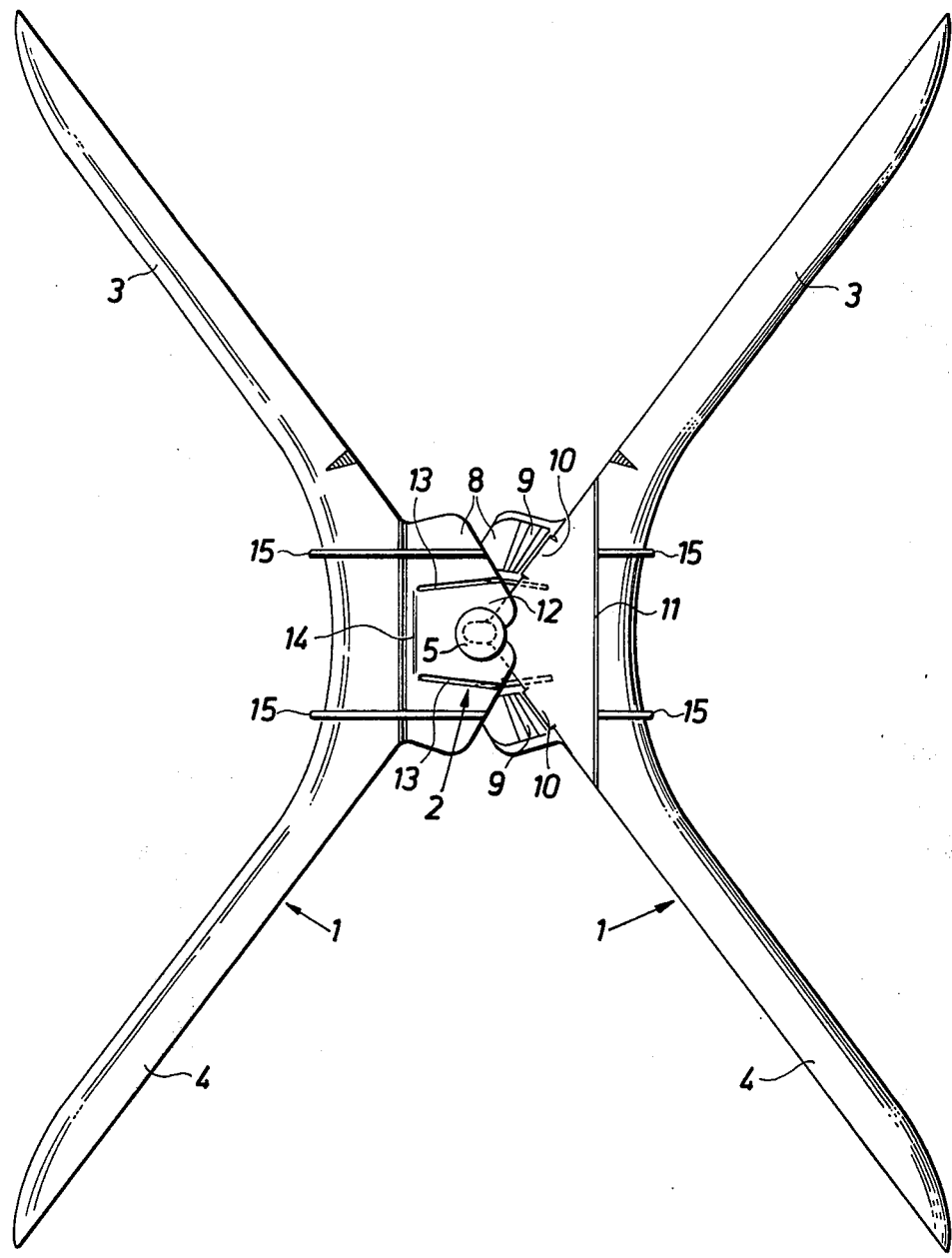
FIG. 1 is a side view of the speculum composed of two angle pieces, it being shown with the angle pieces in the mutual pivoting position in which they can be put together and taken apart.

As is apparent from FIGS. 1 – 3, the speculum of the present invention is composed of two angle pieces 1, oscillatably put together at a pivot portion 2. From this pivot portion 2 project four legs 3, 4 of both angle portions. These legs can be moved together or apart in pairs, with one pair 3, 3 or the other 4, 4, serving as handles for the operation of the respective corresponding pair 4, 4 or 3, 3. In FIGS. 2 and 3, the legs 4 are moved together or closed to enable introduction into a bodily cavity, and can thereby be maneuvered by the open pair of legs 3, serving the purpose of handles, and be also actuated by the latter for opening to the required degree to dilate the cavity.

Each angle piece 1 has a U-shaped cross-section for substantially the whole of its length, thus giving the legs a trough-like shape. The ends of the legs are softly rounded off by reducing the profile dimensions in the end portions. The coupled angle pieces have their troughs facing each other so that an inspection channel is formed between a pair of legs not completely closed together.

As a foundation for an embodiment where either leg pair can optionally be used as active operational means is naturally the requirement that the leg pairs have differences in appearance. The legs 3 in the illustrated embodiment are thus narrower than the legs 4.

According to the invention, the angle pieces 1 of the speculum are identically alike. In the area of the pivot portion 2 this sole required type of angle piece 1 is made with a pivot pin 5 on one side and on the other side with a hole 6, which is arranged to accommodate the pin 5 on the identical angle piece to which it is coupled. The pin 5 and hole 6 are located on a common axis at right angles to the chief plane of the angle piece. The pin is provided with a head and is introducable into the hole 6 in the opposing angle piece by means of a slit 7 which, from the outer edge of a projecting side portion 8 in which the hole is situated, leads radially in towards the hole.

On the inside of the side portion 8 there are a plurality of locking teeth 9, which in co-action with a projection 10 on the leg of an opposing angle piece serve to retain the legs in a set open attitude. In order to eliminate the risk of nipping, the locking teeth 9 are located in depressions. The side portion 8 has two groups of such depressed locking teeth, each for co-action with a leg projection 10 on the respective leg 3 and 4 of an opposing angle piece. The locking teeth 9 and the leg projections 10 have sloping co-acting engagement surfaces such that, for an inwardly directed force on the introduced legs urging them together, they strive to keep the side portion provided with the pin together with the side portion 8 on the opposing angle piece. The leg projection 10 on the side of the respective leg provided with the pin is made projecting and somewhat sloping, to enable movement out of engagement substantially simultaneously along the whole of its engagement length in a releasing movement, according to the chain-dotted line in FIG. 8.

The slit 7 is suitably somewhat underdimensioned in relation to the pin 5, so that the pin is retained by a snap action in the hole 6, the corners of the slit also being rounded off to allow coupling together and taking apart.

In FIGS. 1 and 4 it is indicated that the pin 5 has a somewhat flattened cross-section so that when it is about to be introduced into the hole, i.e. when two angle portions are held with their troughs facing each other and with the leg pairs 3, 3 and 4, 4 having the same angle according to FIG. 1, it can be passed through the slit 7 with its least width being the criterion, for the space required. After the pin of one angle piece has been accommodated in the hole of the associated angle piece and vice versa, and the angle pieces have been turned from the coupling attitude to a working attitude, the pins are secured against unintentional disengagement with the holes since the greater width of the pin then comes against the slit 7.

From FIGS. 6 and 7 it is apparent that the pin 5 tapers from base to head, which ensures positive movement if the base dimension of the pin gives a tight fit in the hole 6. This design also provides greater movement between the pin 5 and the side portion 8 in the opposing angle piece when being pressed together across the pivot portion in accordance with what is described in detail hereinafter in conjunction with FIG. 8.

It is further apparent from FIG. 3 that each of the coupled-together angle pieces 1 have the side portion 8 provided with the hole 6 situated outmost, overlapping the portion of the opposing angle piece 1 provided with the pin 5. The side portion 8 of the angle piece is therefore displaced sideways and outwardly so much that the co-acting legs of the coupled side pieces are mutually centered sideways.

A crease or similar folding line 11 is indicated in FIG. 1 on the side of the angle piece 1 behind the pin 5, for the purpose of giving the area in the vicinity of the pin 5 with the leg projections 10 a positive inward movement for releasing the leg projections from engagement with the locking teeth 9 when pressing the pivot portion 2 over the side portions 8. The position of the pin 5 and its adjacent area under the action of such pressure is indicated in FIG. 8 by chain-dotted lines, in this case in an embodiment which is taken to give suitable movement for releasing the leg projection 10 from engagement without such a special folding line. At the same time, the hole 6 can be made outwardly divergent and the head of the pin 5 double convex in axial cross-section to facilitate a certain amount of skew in the pin 5. As is best seen from FIGS. 1, 2 and 5, a part of the side portion 8 is shaped by means of a pair of slits 13 to form a flexible flap 12 provided with the hole 6, the flap being fairly easily flexible along a folding line 14, in relation to the surrounding parts of the side portion 8, which in contradistinction are stiffened up by ridges 15. These ridges pass round to the folding line 11 on the opposite side of the angle piece (FIG. 4), forming finger grip ridges on the spine of the angle piece at the same time. The flexible flap 12 and the side portion 8, otherwise stiffened up in the area of the locking piece 9, enable a positive movement for releasing the leg projections 10 from engagement with the locking teeth 9, when the pivot portion 2 is gripped and compressed with the squeezing force applied on or adjacent to the heads of the pins 5. In order to give the stiffened portions the greatest rigidity, and the flexible flap best flexibility, the slits 13 are arranged to diverge from each other rather heavily, as seen from the folding line 14, the flexible flap thus being made with a small base length and a large area where engagement and force transmission take place.

The angle between the legs 3 and 4 of the angle piece 1 is shown on the drawing to be greater than 90° and is selected, e.g., for a vaginal speculum, to advantage within the range 105° – 120°. In this way, good space is obtained for the hands, and a spacious design of the interior of the pivot portion 2 is enabled, offering rapid expansion of the portion of the inspection channel situated there, as seen against the angular variation when opening the legs 3 or 4, either of which pair having been introduced into the cavity.

The angle piece of the speculum can, as has been shown for the illustrated and described embodiment, be designed so that it can quite well be manufactured in one piece from plastic by injection moulding or the like.

I claim:

1. A speculum arranged for examining body cavities and consisting of two angle pieces (1) each having a generally U-shaped cross-section along substantially the whole of its length, and consequently having trough-like legs (3, 4) of which one leg (3) is preferably narrower than the other (4), both angle pieces (1) with their troughs facing each other being removably connectable to each other with side portions of the angle pieces on either side of the speculum overlapping each other to form a pivot portion (2), from which the four legs (3, 4) extend, being movable together or apart by means of one pair of legs (3, 4), one from each angle piece (1), serving as handles for operating the other pair (4, 3), characterized in that both angle pieces (1) are made identically alike and that in the area of the pivot portion (2) each has on one side a pin (5) and on the opposite side a hole (6), the hole in each angle piece (1) being made to accommodate the pin (5) of the opposing angle piece (1) for creating the pivoting function of the pivot portion (2).

2. A speculum as claimed in claim 1, characterized in that the pin (5) on either angle piece (1) is arranged on the outside of the said one side portion thereof and is made with a head, and that the hole (6) which is arranged in the other side portion (8) thereof merges into a radially outwardly directed slit (7) breaking through the edge of said other side portion (8) for inserting the pin of the opposing angle piece (1).

3. A speculum as claimed in claim 2, characterized in that the slit (7) is somewhat underdimensioned in relation to the pin (5) so that the pin is retained snapped in the hole (6).

4. A speculum as claimed in claim 2, characterized in that the width of the pin (5), transverse to the insertion direction in the slit (7) at a predetermined insertion orientation is narrower than the width of the pin in the insertion direction so that after mutual turning of the angle pieces (1) the pin is prevented from leaving the hole (6) via the slit (7).

5. A speculum as claimed in claim 2, characterized in that the pin (5) tapers from its base to its head, its base dimension being such as to conform with a tight fit to the diameter of the hole (6), or the least diameter thereof in the case where the hole dilates outwardly.

6. A speculum as claimed in claim 2, characterized in that the side portion (8) provided with hole (6) of both coupled side portions (1) overlaps on either side of the speculum the side portion of the angle pieces provided with the pin (5), the side portion (8) provided with the hole on each angle piece being made displaced sideways such that both the co-acting leg pairs (3, 3; 4, 4) of the angle pieces are mutually centred sideways.

7. A speculum as claimed in claim 2, in the case where the side portions (8) provided with the holes (6) have locking teeth (9) for fixing the angular position of the angle pieces (1) in co-action with leg projections (10) on the opposing angle piece, characterized in that a part of the respective side portion (8) provided with said hole (6) is made as a flap (12) by means of a pair of slits disposed on either side of the hole (6), the flap preferably provided with a folding line (14) at its base so that the remainder of the side portion (8) with the locking teeth (9) can remain substantially unaffected by axial compression of the pivot portion (2) via the flaps (12) for releasing the leg projections (10) from engagement with the locking teeth (9).

8. A speculum as claimed in claim 7, characterized in that a folding line (11) is arranged on the side portion of the angle piece behind the pin (5) so that when the pivot portion (2) is axially compressed the leg projection (10) is given a definite inward movement to release it from engagement with the locking teeth (9).

* * * * *